United States Patent [19]

Nambu et al.

[11] Patent Number: 4,828,493
[45] Date of Patent: May 9, 1989

[54] DENTURE BASE

[75] Inventors: Masao Nambu, Yokohama; Osamu Kuwabara, Kamakura; Yoshihiko Okuno, Osaka; Toshiyuki Ohban, Osaka, all of Japan

[73] Assignee: Nippon Oil Co., Ltd., Japan

[21] Appl. No.: 209,419

[22] Filed: May 24, 1988

[30] Foreign Application Priority Data

Nov. 14, 1985 [JP] Japan ............................ 60-253685
Dec. 18, 1985 [JP] Japan ............................ 60-283096

Related U.S. Application Data

[63] Continuation of Ser. No. 930,697, Nov. 13, 1986, abandoned.

[51] Int. Cl.[4] .............................................. A61C 13/00
[52] U.S. Cl. ................................. 433/199.1; 264/17; 106/35
[58] Field of Search ................. 433/199.1; 106/35; 264/17, 18

[56] References Cited

U.S. PATENT DOCUMENTS 2,551,812  5/1951  Nelson ............................ 433/199.1
3,628,988 12/1971  Stol et al. ........................ 433/199.1

FOREIGN PATENT DOCUMENTS 56446   3/1984  Japan .
497179 12/1938  United Kingdom ............. 433/199.1

OTHER PUBLICATIONS

"Polymer Application" by Masao Nambu, vol. 32, page 523 (1983).

Primary Examiner—John J. Wilson
Attorney, Agent, or Firm—Majestic, Parsons, Siebert & Hsue

[57] ABSTRACT

A denture base contains an elastic support for supporting at least one artificial tooth and fittings fixed to the elastic support for removably positioning the denture base. The elastic support is made of a hydrogel prepared by a process comprising a casting step of casting into a mold an aqueous solution containing more than 5 wt % and not more than 40 wt % of a polyvinyl alcohol having a degree of hydrolysis of not less than 95 mol % and an average polymerization degree of not less than 700, a freezing step of cooling the cast aqueous solution to a temperature of not higher than − (minus) 10° C. to obtain a frozen mass, a thawing step of thawing the frozen mass, and one to seven additional cyclic processing steps each including the freezing and thawing steps.

14 Claims, 1 Drawing Sheet

DENTURE BASE

This is a continuation of application Ser. No. 930,697 filed Nov. 13, 1986, and now abandoned.

BACKGROUND OF THE INVENTION

1. Field of the Invention

The present invention relates to a process for producing a denture base, and more particularly to a process for producing an elastic and removable denture base made of a hydrogel which denture base may be removed as desired, for example, while the user is sleeping in bed.

2. Related Art Statement

It is well known that a denture base is one of the important constitutional elements of a removable denture. Such a denture base serves as a base or support for supporting an artificial tooth or teeth by covering mucosa of alveolar crista and gingival mucosa, thereby to transmit occlusal pressure (functional pressure) to gingival mucosa and to disperse chewing reaction evenly.

Known materials for such a denture base include cobalt-chromium alloys, palladium alloys, platinum added with gold, and acrylic resins. However, since these known materials are hard, they often cause rubefaction, pain or inflammation of mucosa around and below the denture base with foreign body feeling, as well as inflammation or pain of mucosa of allveolar crista, pain of alticulatio of maxillae, inflammation of proglossis, abnormal growth of tunica mucosa oris or caries of the remaining (healthy) teeth. In a case where plural teeth remain, a removable partial denture is set between the remaining healthy teeth to fill the defect, this being referred to as a partial prosthesis system. However, in such a partial denture, it is often desired that the base surface area of the denture base is larger than the occlusion surface area of the artificial teeth so that the major portion of the defect alveolar crista is covered by the base portion of the denture base. However, since a denture base having a shape and dimensions enough to fully cover the lost alveolar crista cannot be inserted through the space formed between the occlusion surface of the remaining teeth, such a denture base is not adapated for easy attachment and removal. Under such circumstances, the base surface area of a removable denture base should be decreased to have the dimensions approximate to those of the occlusion surface area to leave some gaps between the denture base and the remaining teeth, leading to detrimental results that the food remaining in these gaps are putrefied to cause caries of the remaining healthy teeth or gingivitis, in addition to serious detraction of the appearance of the denture base.

A partial denture base having a base portion larger than the occlusion surface area may be produced by using a resilient and elastic material, such as rubber, in lieu of metals, alloys or hard synthetic resins. However, the known rubber materials which have been used for such purpose, including vulcanized natural rubber and synthetic rubbers, not only have unpleasant rubber taste and foreign body feeling but also irritate the oral mucosa (mucosa covering alveolar crista and mucosa of palatum durum) and proglossis to induce inflammation of these tisues. A more serious problem of the rubber base materials is that they are rapidly deteriorated by the attack of oils and fats contained in the foods to loose its mechanical strength or to be decomposed to loose its integrity.

OBJECTS AND SUMMARY OF THE INVENTION

An object of this invention is to provide a process for producing a denture base made of waterproof and oil-resistant hydrogel which is excellent in compatibility with the living tissues not to irritate the oral mucosa and has no unpleasant taste and odor due to plastics, rubber or metals so as not to provide foreign body feeling or pain to the mucosa of alveolar crista or the living tissue surrounding the alveolar crista.

Another object of this invention is to provide a process for producing a denture base which is larger than the occlusion surface area and yet which can be elastically deformed so as to be easily inserted through the space between the remaining healthy teeth and can be snugly fitted on the desired position.

A further object of this invention is to provide a process for producing a denture base which does not cause infection due to putrefaction when it is continuously held in position.

With the aforementioned objects in view, the present invention provides a process for producing a denture base comprising an elastic support made of a hydrogel for supporting at least one artificial tooth, and fitting means fixed to the elastic support for removably positioning the denture base in situ, which process comprises a casting step of casting an aqueous solution containing more than 5 wt% and not more than 40 wt% of a polyvinyl alcohol having a degree of hydrolysis of not less than 95 mol% and an average polymerization degree of not less than 700 into a mold having desired shape and dimensions, a freezing step of cooling the cast aqueous solution to a temperature of not higher than −(minus) 10° C. to obtain a frozen mass, a thawing step of thawing the frozen mass, and one to seven additional cyclic processing steps each including the freezing and thawing steps.

DESCRIPTION OF THE INVENTION

Figure 1:
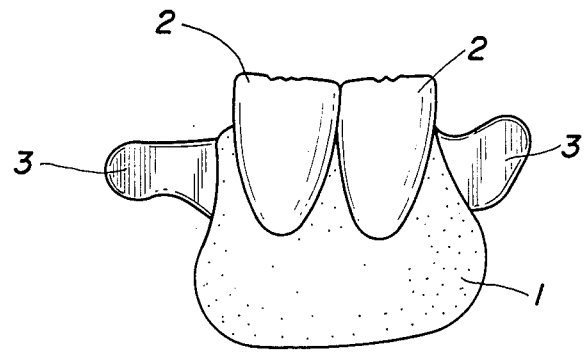
FIG. 1 is a perspective view showing an embodiment of the denture base according to this invention.

Details of the hydrogel used in this invention are disclosed by Masao Nambu, "Polymer Application", vol. 32, page 523 (1983), Japanese Patent Laid-Open Publication No. 56446/1984 and pending Japanese Patent Application No. 54330/1984 filed on Mar. 23, 1984.

The polyvinyl alcohol used as the material for the hydrogel in the invention should have a degree of hydrolysis of not less than 95 mol%, preferably not less than 98 mol%. It is also essential that the polyvinyl alcohol has an average polymerization degree of not less than 700. A polyvinyl alcohol having a polymerization degree of about 800 to 3,300 may be used in this invention, and it is recommended to use a commercial product having a polymerization degree of from 1,000 to 2,600.

According to the present invention, an aqueous solution containing the aforementioned polyvinyl alcohol is prepared at the initial step. The concentration of polyvinyl alcohol in the solution should be within the range of more than 5 wt% and not more than 40 wt%, preferably from 20 to 35 wt%. If the content of polyvinyl alcohol is less than 5 wt%, the resultant hydrogel (elastic rubber-like material of high water content) becomes too soft not to fulfil the required functions (fixation of artificial teeth and prevention of movement and sinking of the implanted artificial teeth). On the contrary, if the content of polyvinyl alcohol exceeds 40 wt%, the resultant hydrogel becomes too hard to have unsatisfactory elasticity, leading to detrimental results similar to those of the conventional metallic or hard plastic materials.

In the next step, the aqueous solution of polyvinyl alcohol is cast in a mold for molding a desired denture base. A gypsum mold prepared by the normal dental technic may be used, and a mold made of a silicone resin may also be used conveniently.

The cast aquesous solution of polyvinyl alcohol is then cooled to a temperature of not higher than − (minus) 10° C. to freeze the aqueous solution and subsequently the frozen mass is thawed. The sequential freezing and thawing steps are repeated for 2 to 8 times to prepare a denture base made of the hydrogel used in the invention. Although the hardness of the hydrogel or rubber-like elastomer is increased as the number of repeated freezing-thawing cycles is increased, the increment in hardness and strength of the gel becomes smaller with the increase of the repeated cycles and the merit obtainable by an additional cycle is not so great as to add a further processing after the ninth cycle (see Masao Nambu, "Polymer Application", vol. 32, page 523 (1983)). In view of the foregoing, it is economically advisable to process the frozen mass of aqueous polyvinyl alcohol solution for additional 1 to 7 repeated cycles.

After the completion of repeated freezing-thawing processing, the gypsum mold is opened using a gypsum forceps or electric drill to remove the molded denture, i.e. the composite molded article including the artificial teeth and the denture base support of the invention. It is noted here that one or more artificial teeth are embedded in the gypsum mold prior to casting of the aforementioned aqueous polyvinyl alcohol solution, so that the composite molded article including the artificial teeth and the denture base support portion is produced by the aforementioned sequential steps. The material for the artificial teeth may be selected from the conventional materials, such as polymethylmethacrylate resin, silver/gold/palladium alloy, platinum added with gold, cobalt/chromium alloy, nickel/chromium alloy, stainless steel and ceramics. In order to ensure firm bonding between the artificial teeth and the denture base support made of a hydrogel, anchor cavities are formed on the sides of the artificial teeth so that these cavities are filled with the aqueous solution of polyvinyl alcohol to be solidified therein to fix the artificial teeth firmly in the desired positions.

In general, a denture is composed of artificial teeth, a saddle or plate, a mechanism for coupling or fixing the artificial teeth with the saddle or plate, and an additional mechanism referred to as retainer or connector in the prosthetic dentistry. The artificial teeth may be bonded and fixed to the denture base support, e.g. the saddle or plate, by the anchoring function of the solidified hydrogel contained in the cavities at the base portions of the artificial teeth, as described above. The number of the cavities and the shape and dimensions of each cavity may be determined, without any particular restriction, in compliance with the clinical requirements and in consideration of the dimensions of the implanted teeth. Each artificial tooth may be provided with a number of small pores which cross with each other internally of the base portion of the tooth so that it is firmly fixed to the denture base support.

The retainer is a mechanism for retaining the denture in a desired position in the oral cavity, and a removable denture must be provided with a tough retaining mechanism which may be removed by the fingers of the user. The denture base, according to the present invention, has a clasp or attachment for removably connecting and fixing the same to the remaining healthy teeth or to connector means fixed to the remaining teeth. As such fitting means for removably positioning the denture base or for detachably retaining the denture base, any of the known means may be adopted, the examples being metal wire or cast metal hooks including annular hooks, extended hooks, twin hooks and continuous hooks, a bar type joint such as Dolder bar joint comprising a half-split cylinder and a bar to be snapped in the half-split cylinder, and a ball socket hinge wherein a spherical ball is hooked by a socket. Such a retainer may be attached to the denture base of the invention by mounting the same to the gypsum mold prior to the casting step, or may be attached to the denture base after it is molded, similarly as in the production of conventional removable denture bases. The connector is a mechanism for connecting scattered plural dentures for filling separated defects in the arcus dentalis, and generally made of a metal bar or plate. Such a connector may be, of course, combined with the present invention so that plural dentures are prepared and then connected by a connector of alternatively a group of connected dentures may be prepared by using a gypsum mold of special design.

The support of the denture bae and the artificial teeth may be ground by a rotary grinder, if necessary.

The denture base prepared in accordance with this invention may be dipped in an antiseptic solution used for sterilizing the fingers, the sclera of oculus, the cornea and the urethra, such as chlorhexidine (Hibitane, Registered Trade Mark) or benzalkonium chloride (Osvan, Registered Trade Mark), followed by rinsing with water to be applied for practical use. According to a further aspect of this invention, an antiseptic solution may be added to the aforementioned aqueous solution of polyvinyl alcohol which is then subjected to the repeated freezing-thawing operations to form the hydrogel. The thus formed hydrogel may be rinsed with water and applied for use.

The hydrogel forming the support of the denture base of this invention is an opaque white rubber-like elastomer which may be colored to have a color tone resembling the soft tissues, such as the gingiva or alveolar crista, in the oral cavity to improve its appearance. For this purpose, one or more edible dyestuffs may be selectively used or mixed together to prepare a denture base having a desired color tone. Examples of edible dyestuffs which may be used in the denture base of this invention include aluminum compounds of Food red Nos. 2 and 3, Food yellow Nos. 4 and 5, Food green No. 3 and Food blue Nos. 1 and 2. These dyestuffs may be added to the aqueous solution of polyvinyl alcohol prior to the preparation of the denture base of the invention.

Since the denture base of the invention is made of a hydrogel, i.e. a gel of high water content, resembling the soft tissues and no harmful chemical agent is used as the gelling agent, it is excellent in affinity with the oral mucosa (excellent in compatibility with living tissues). In addition, the support of the molded denture base, according to this invention, is elastic and thus may be resiliently deformed to be readily inserted through a gap formed between the biting surface areas of the remaining healthy teeth to be fitted in desired position. Although the support of the denture base is somewhat deformed by biting actions since it is made of an elastic material, the denture base is restored to have the initial shape and dimensions immediately after the loading or stress by the biting action is released. The prosthetic object of compensating the defected appearance can be attained, with the provision of sufficient occlusal pressure, by the use of the denture base of the invention. Particularly when the denture base of the invention is combined with the remaining teeth and retainer means by utilization of partial prosthetic technique, the function of once completely lost tooth can be recovered to a considerable level. More specifically, a variety of foods, such as bean-jam bun, toasted bread, KONNAKU (devil's tongue), fish-shaped pancake filled with bran jam, Japanese hotchpotch and TEMPURA of a pawn or vegetables, can be bitten by the denture produced in accordince with this invention, without any special care to protect the same. Even if a piece of roast meat, such as beef or pork, contacts directly with the occlusion surface of the denture, the denture base of this invention is elastically deformed so that the artificial teeth supported thereby are tentatively inclined outwards under the occlusal pressure, but no pain is caused in any of the living tissues in the oral cavity and the artificial teeth are spontaneously restored to the initial positions by the elastic nature of the denture base support. As a result, although the roast meat cannot be bitten directly by the denture produced by this invention, such a hard meat can be pushed to and then bitten by the remaining healthy teeth conveniently.

Contrary to the conventional materials for the denture base support, the support of the denture base according to this invention does not cause foreign body reaction with the living tissues, infiltration into cells, growth of glanuloma, formation of ulcer or necrosis of living tissue. (In this connection reference should be made to Masao Nambu, "Polymer Application" vol. 32, page 523 (1983); Masao Nambu, JETI, vol. 33, (9), page 45 (1985); Y. Honda, M. Nambu et al., Am. J. Ophthalomology, vol. 100, page 328 (1984) and vol. 99, page 492 (1985); and Kohichi Tamura, Masao Nambu et al., "Artificial Organs", vol. 13, page 1197 (1984).)

In the present invention, a denture base made of a hydrogel containing 70 to 94 wt% of water may be easily prepared. Nevertheless this hydrogel is a rubber-like elastomer excellent in mechanical strength, it behaves as though it were pure water because of its high water content, and thus the damages of the living tissues are suppressed to appreciable level. In preparation of the denture base of this invention, chemical reagents, such as acids, alkalis, peroxides, sulfur-containing compounds or nitrogen-containing compounds and organic solvents are not used at the step of forming the gel of aqueous polyvinyl alcohol solution, and no plasticizer and/or stabilizer is necessary. In view of the fact that the main cause for the conventional medical materials to damage the living tissues is the presence of chemicals or organic solvents contained in the finished products or the presence of plasticizers or stabilizers added to the starting materials, the denture base of the present invention which is made of a hydrogel prepared without the use of such a harmful ingredient is remarkably superior over the denture bases made of conventional materials.

The compatibility with living tissues of the hydrogel used in the present invention was investigated by the following experiments. An aqueous solution of polyvinyl alcohol was coated on a sterilized glass plate using an applicator to form a 0.3 mm thick coating which was subjected to four repeated cycles of the freezing-thawing steps, according to this invention, whereby a hydrogel film having the dimensions of 2 cm×2.3 cm×0.3 mm was prepared. An adult mongrel having a weight of 17 kg was put under general anesthesia by admistering with pentothal sodium through intravenous injection, and the skin covering the right top head was opened along a longitudinal direction after removing the hair from the head skin, followed by removal of the muscle temporalis. The head bone was then pierced using a drill and a defect as large as a hen's egg was formed using a bone forceps. The dura mater was resected to form a 1.5 cm×2 cm opening over which the aforementioned hydrogel film was applied, and the four corners of the hydrogel film were sutured, followed suturing of the muscle and the head skin.

After the lapse of six months, the hydrogel film and the surrounding dura mater and cerebral parenchyma were extracted from the killed mongrel, and the haematoxylin-eosin stain specimen was examined through visual observation and through optical microscope observation. The result was that no adhesion between the hydrogel film and the surface of brain was observed. The surfaces of the hydrogel were surrounded by an encapsulating tissue, but the adhesion to the pia mater was not observed and no infiltration of cells and no-growth of glia cells were observed. This result shows that the material, i.e. the hydrogel, used for forming the support of the denture base of the present invention is inert to the living tissues including the surface tissue of brain and the dura mater.

After dipping a 5 cm×5 cm×0.3 mm film made of the same material as used in the denture base of this invention in a Hibitane (hydrochloride) solution, the film was rinsed with a sterilized physiological saline solution. The chest of an adult mongrel having a weight of 13 kg was opened under anesthesia by intravenous injection of pentobarbital, and the pericardium of the left ventricle was resected to form a large opening such that only a slim margin for suturing was left. The opening was covered by the aforementioned hydrogel film (5 cm×5 cm×0.3 mm).

The extracted specimen of the covered portion resected from the killed mongrel after feeding for six months from the operation was examined visually and through an optical microscope and a scanning electron microscope to reveal that no adhesion of the covering film to the heart was observed and that the surfaces of the hydrogel film were smoothly covered by endothelium tissue. No particular cell reaction from the viewpoint of pathological histology was observed, other than a thin endothelium tissue growing at the side of the heart.

The chest of an adult mongrel was opened to form a defect at the muscular portion of the diaphragm, and the defect was covered by the same hydrogel film (4 cm×6 cm×0.3 mm). After feeding the mongrel for six months, the mongrel was killed and the covered portion was extracted to prepare a specimen which was examined to reveal that no adhesion between the covering hydrogel and the lung was found. Although the hydrogel film was covered with thin fibrous tissues, no appreciable tissue reaction was found. This result shows that the hydgrogel film is inert to the soft living tissues including epicardium, pericardium, fibrous epicardium and diaphragm.

A contact lens shape arcuated membrane made of the same hydrogel and having a thickness of 0.2 mm, a radius of curvature of 8 mm and a diameter of 13 mm was prepared and fitted on a cornea of oculusof a volunteer. After fitting the arcuated membrane for 15 hours, the membrane was removed from the cornea which was instillated with fluorescein immediately after the removal of the membrane. The cornea was examined through a slit lamp microscope to reveal that no part of the cornea was stained. This result shows that the used hydrogel does neither hinder the respiration of the cornea nor damage the cornea, since it contains a large amount of water and thus enriched in solubility for oxygen.

As should be appreciated from the foregoing, the hydrogel used in this invention causes no abnormal reaction at least within the time period of six months even when it is used in prosthesis of a defect formed in a body portion which is sensitive to a foreign body, such as the dura mater encephali, the pericardium and the diaphragm. It should be also appreciated that the hydrogel used as the material for the denture base of the invention is exceedingly inert to the soft living tissues, this being revealed by the result that no abnormal reaction was found in a cornea which has been contacted with the hydrogel for a period of more than half day notwithstanding the fact that the cornea is sensitive to a foreign body and very easily damaged by insufficient supply of oxygen and by the contact with a hard foreign body. As will be described hereinafter in the examples, the material for the denture base used in the present invention could be used without any serious objection even after it had been repeatedly contacted with the oral mucosa over a period of nine months.

As has been described hereinbefore, the denture base prepared in accordance with this invention may be applied for practical use after it is dipped in an antiseptic solution, such as chlorhexidine or Osvan, and then rinsed with water. Although the major portion of the antiseptic solution is rinsed out by the subsequent step of rinsing with water, a trace quantity thereof is adsorbed and firmly trapped by the hydrogel to exert antiseptic or sterilizing function over the bottom surface (the surface opposed to the impression model) and the ground side surfaces of the support portion, i.e. the sides opposing respectively to the tongue and the cheek. As the result of this antiseptic function of the trace antiseptic agent, the denture base is kept clean for a long time. Chlorhexidine and Osvan are well known chemicals for cleaning the oral cavity (see Japanese Patent Publication No. 42764/1985; and Toshiyuki Nambu et al., "Collection of lectures in the Meeting of Japan Biomaterial Society", page 222 (1982)), for sterilizing soft contact lens (see Kazumi Ogata (edited by Saburo Hayano), "Ophthalmologic MOOK", vol 2, page 230 (1978), published by Kanehara Shuppan K. K.), and for sterilizing the tunica conjunctiva and the cornea of the oculus (see "Encyclopedia of Pharmacology by Goodman-Gilman", the last volume, page 1301 (1974), published by Hirokawa Shuppan K. K.). As has been described hereinabove, the sterilizing effect of such chemicals is retained for a long time when the denture base of this invention is sterilized thereby. This is a further advantage of the denture base provided by this invention, since one of the disadvantages of the synthetic resins used as the materials for the conventional denture bases is contamination by bacteria.

The hydrogel used in the present invention is a hydrophilic gel containing a large amount of water, and resisting swelling and deterioration by the attack of fatty substances. Even when the material used in this invention is dipped in an edible oil, such as soybean oil, under a loading of pulling stress for a long time, the stress relaxation observed in the material is equivalent to that observed when it is dipped in water. This is quite different from the case where a silicone rubber or a vulcanized natural rubber is subjected to the similar tests. When a silicone rubber or a vulcanized natural rubber is dipped in a soybean oil under a loading of stress, serious stress relaxation is resulted within 30 minutes and such a conventional material is deteriorated to become fragile and to be easily broken.

EXAMPLES OF THE INVENTION

The present invention will be described more specifically with reference to some examples thereof.

Example 1

A 30 wt% aqueous solution of a polyvinyl alcohol having a degree of hyrolysis of 98 mol% and an average polymerization degree of 1,400 was cast into a gypsum mold for molding a denture which was to be filled in a defect formed on the submaxilla. The cast solution was allowed to stand for 2 hours at − (minus) 30° C. to freeze the same. The resultant frozen mass was then thawed. The freezing and thawing operations were repeated for five cycles, and then the mold was broken using a gypsum forceps and an electric drill to remove the molded article from the mold. The molded article was an embodiment of the denture having the denture base according to this invention, as shown in FIG. 1. The denture comprises an artificial teeth 2, a denture base including a support 1 for supporting the artificial teeth 2, and metal fittings or rests 3 which serve as the retaining means upon fitting on the adjacent remaining healthy teeth.

The support 1 of the denture base was ground by an electric grinder, and the entire denture was dipped in a 0.2% aqueous solution of Hibitane and then rinsed with a large quantity of tap water for about 4 hours.

Figure 2:
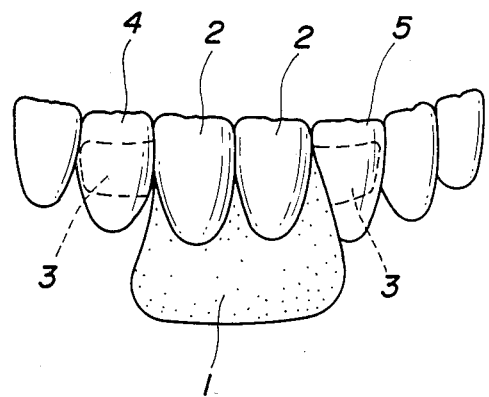
FIG. 2 is a schematic illustration showing the denture base of FIG. 1 fitted between the remaining healthy teeth.

The support 1 of the denture base could be easily deformed so that it could be inserted by the user without the need of any aid by an assistant into the defect between the remaining teeth 4 and 5 (see FIG. 2) along the vertical direction. The denture was snugly fitted in the defect with good appearance, and the unpleasant feeling caused by the fitted denture was so little as though a small mass of chewing gum was present in the oral cavity. The denture had been used satisfactorily under the aforementioned condition. The denture was fitted over a period of 270 days in such manner that it was continuously fitted for 15 hours a day and stored in water when it was removed from the oral cavity. The denture did not irritate the proglossis and did not cause pain when it was used for biting foodstuffs, with no unpleasant feeling due to the presence of a foreign body in the oral cavity. Neither inflammation of the Palatum nor abnormal growth of the oral mucosa were caused by the denture of this example, and the quantity of stegnant leftments of foodstuff remained below a normal level. The denture did not cause rubefaction or inflammation of the mucosa around and below the denture base, inflammation of the gingiva around the collum dentis, causalgia within the oral cavity, color change of the base, periodentitis at the collum dentis of the hooked tooth, fracture of the tooth crown due to decay of the hooked tooth, pulpitis, paradentitis at the radix dentis, hypersensitiveness of the remaining teeth, inflammation or pain of the mucosa of the alveolar crista or the portions at the vicinity of the alveolar crista, or pain of the alticulatio of maxillae.

Example 2

The dynamic modulus of elasticity of the material used in the denture as described in Example 1 was measured to find that the dynamic modulus of elasticity was $5 \times 10^5$ Nm$^{-2}$ (at 37° C.). The material for the denture base of this invention is harder than the smooth muscle of the small intestine ($2 \times 10^4$) and softer than the vulcanized natural rubber ($1.5 \times 10^6$), the nitrile rubber ($1.2 \times 10^6$), the tendon ($10^8$), the collagenous fibre ($10^8$), the hair ($10^9$) and bones ($10^8$ to $10^{10}$). The material for the denture base of this invention is a highly elastic material comparable to the smooth muscle of the blood vessel ($10^5$, J. Krufka, Am. J. Physiol., 125, 1 (1939); D. H. Bergel, J. Physiol., 156, 445 (1961); T. Tanaka et al., J. Biomechanics, 7, 357 (1974); Masamitsu Hasegawa et al., Journal of Japanese Rheological Society, 9, 8 (1981)) and also comparable to the cartilage ($5.8 \times 10^5$ to $160 \times 10^5$, J. C. Bray et al., J. Biomed. Mater. Res., 7, 431 (1973); D. M. Gore et al., Phys. Med. Biol., 28, 233 (1983)).

In view of the fact that a hard material, such as polyethylene having a dynamic modulus of elasticity ranging within $10^8$ to $10^9$ Nm$^{-2}$, tend to damage the living tissues, there is a demand for a highly elastic material resembling the soft living tissues. (In this connection, reference should be made to Mitsunobu Yamamoto, "Clinical Physiology", 6, 504 (1976); Satoru Kosaba, Kazuyuki Yagi et al., "Artificial Organs", 11, 1162 (1982); Takashi Teramatsu et al., "Artificial Organs", page 257 (1983), published by Nankodo; Mitsunobu Yamamoto, "Proceeding of Medicine" 105, 477 (1978); and Hiroshi Moriaki et al., "Artificial Organs", 8, 81 (1979).) As has been described hereinabove, the material used in the denture base according to this invention has a dyanamic modulus of elasticity in compliance with the required elasticity. Although a certain silicone rubber has a dynamic modulus of about $5.5 \times 10^5$ and has a satisfactorily high elasticity comparable to those of the soft living tissues, the elasticity of the silicone rubber is deteriorated such that stress relaxation proceeds abruptly after the lapse of a few minutes to lower the tensile strength to 1/100 of the initial tensile strength after 9 to 25 minutes when the silicone rubber is dipped in soybean oil maintained at 37° C. while it is elongated by 5%. This is contrary to the fact that the same stress applied to the same silicone rubber is only slightly relaxed even after the lapse of 10 hours when it is dipped in water. In contrast thereto, when the material, i.e. the hydrogel, used in the denture base of this invention is subjected to tests for learning the relaxation of stress both in water and soybean oil (at 37° C.), the decrease in stress after the lapse of 10 hours in 21% in water and 20% in soybean oil, which corresponds to the decrease in stress of the silicone rubber dipped in water. The test results described above reveal that the material used in the denture base of this invention is a distinctive elastomer which is excellent in waterproof and oil-resistant properties and resembling the soft living tissues.

As will be apparent from the foregoing, the present invention provides a denture base made of a hydrogel which is excellent in compatibility with living tissues and has a good appearance to serve as satisfactory retainer means with good retaining and fitting force and satisfactory durability.

Although the present invention has been described with reference to the specific examples, it should be understood that various modifications and variations can be easily made by those skilled in the art without departing from the spirit and scope of the invention. Accordingly, the foregoing disclosure should be interpreted as illustrative only and not to be interpreted in a limiting sense. The present invention is limited only by the scope of the following claims.

What is claimed is:

1. A process for producing a denture base comprising an elastic support made of a hydrogel for supporting at least one artificial tooth, and fitting means fixed to said elastic support for removably positioning said denture base in situ, which process comprises a casting step of casting an aqueous solution containing more than 5 wt% and not more than 40 wt% of a polyvinyl alcohol having a degree of hydrolysis of not less than 95 mol% and an average polymerization degree of not less than 700 into a mold having desired shape and dimensions, a freezing step of cooling the cast aqueous solution to a temperature of not higher than − (minus) 10° C. to obtain a frozen mass, a thawing step of thawing said frozen mass, and one to seven additional cyclic processing steps each including said freezing and thawing steps.

2. The process for producing the denture base according to claim 1, wherein said artificial tooth is made of a material selected from the group consisting of polymethylmethacrylate resins, silver/gold/palladium alloys, platinum added with gold, cobalt/chromium alloys, nickel/chromium alloys, stainless steel and ceramics.

3. The process for producing the denture base according to claim 1, wherein said artificial tooth is formed with anchor cavities which are filled with said aqueous solution of polyvinyl alcohol so that each artificial tooth is firmly fixed by the solidified hydrogel contained in said cavities.

4. The process for producing the denture base according to claim 3, wherein said anchor cavities comprise a plurality of small pores extending through the base portion of said artificial tooth and crossing with each other internally of said base portion of said artificial tooth.

5. The process for producing the denture base according to claim 1, wherein said fitting means comprises a pair of hooks made of a material selected from the group consisting of a metal wire and a cast metal.

6. The process for producing the denture base according to claim 1, wherein said fitting means comprises a pair of Dolder bar joints.

7. The process for producing the denture base according to claim 1, wherein said fitting means comprises a pair of ball socket hinges.

8. The process for producing the denture base according to claim 1, wherein said fitting means is mounted to said mold prior to said casting step so that said fitting means is attached to said support after said aqueous solution of polyvinyl alcohol is solidified to form said hydrogel.

9. The process for producing the denture base according to claim 1, wherein said fitting means is attached to said support after said hydrogel is formed.

10. The process for producing the denture base according to claim 1, wherein said elastic support is colored by adding at least one edible dye to said aqueous solution of polyvinyl alcohol.

11. The process for producing the denture base according to claim 1, wherein said denture base is sterilized.

12. The process for producing the denture base according to claim 11, wherein said denture base is sterilized by dipping the finished denture base is an antiseptic solution.

13. The process for producing the denture base according to claim 11, wherein said denture base is sterilized by adding an antiseptic solution to said aqueous solution of polyvinyl alcohol.

14. A process for producing the denture including a plurality of denture bases as claimed in claim 1, wherein said denture bases are combined together by means of a connector or coupler to form an integral denture.

* * * * *